(12) United States Patent
Daoud et al.

(10) Patent No.: US 8,250,902 B2
(45) Date of Patent: Aug. 28, 2012

(54) SYSTEM AND METHOD FOR MEASURING AERATION OF A LIQUID

(75) Inventors: Mohamed I. Daoud, Dunlap, IL (US); Dong Fei, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 486 days.

(21) Appl. No.: 12/472,496

(22) Filed: May 27, 2009

(65) Prior Publication Data
US 2010/0300557 A1    Dec. 2, 2010

(51) Int. Cl.
*G01N 29/02* (2006.01)
(52) U.S. Cl. .................. 73/19.03; 73/19.01; 73/19.1
(58) Field of Classification Search ............ 73/19.01, 73/19.03, 19.1
See application file for complete search history.

(56) References Cited

U.S. PATENT DOCUMENTS

| | | | |
|---|---|---|---|
| 3,974,681 A * | 8/1976 | Namery | 73/600 |
| 3,974,683 A * | 8/1976 | Martin | 73/865.5 |
| 4,689,986 A * | 9/1987 | Carson et al. | 73/19.03 |
| 4,825,688 A | 5/1989 | Kraus et al. | |
| 4,934,191 A * | 6/1990 | Kroening et al. | 73/592 |
| 5,454,255 A * | 10/1995 | Kraus et al. | 73/19.03 |
| 5,824,881 A * | 10/1998 | Shouldice et al. | 73/19.1 |
| 6,210,580 B1 * | 4/2001 | Wickins | 210/614 |
| 6,758,187 B2 | 7/2004 | Waters | |
| 7,059,169 B2 | 6/2006 | Cummings et al. | |
| 7,130,738 B2 | 10/2006 | Ha | |
| 7,523,640 B2 * | 4/2009 | DiFoggio et al. | 73/19.03 |
| 7,921,691 B2 * | 4/2011 | DiFoggio et al. | 73/19.03 |
| 2008/0297766 A1 | 12/2008 | Gengler et al. | |

OTHER PUBLICATIONS

Air-X: On-Line Aeration Monitoring Equipment, 5 pages, Viewed at http://www.anst.ca/download/AirXBrochureNA2006.pdf on May 27, 2009.

* cited by examiner

*Primary Examiner* — Hezron E Williams
*Assistant Examiner* — Rodney T Frank
(74) *Attorney, Agent, or Firm* — Finnegan, Henderson, Farabow, Garrett & Dunner LLP

(57) ABSTRACT

A system and method for measuring aeration of a liquid in a liquid channel operates by sending an ultrasonic wave into a liquid channel, receiving a signal corresponding to the echo from the liquid channel and calculating a level of aeration of the liquid in the liquid channel based on the reflected signal.

11 Claims, 7 Drawing Sheets

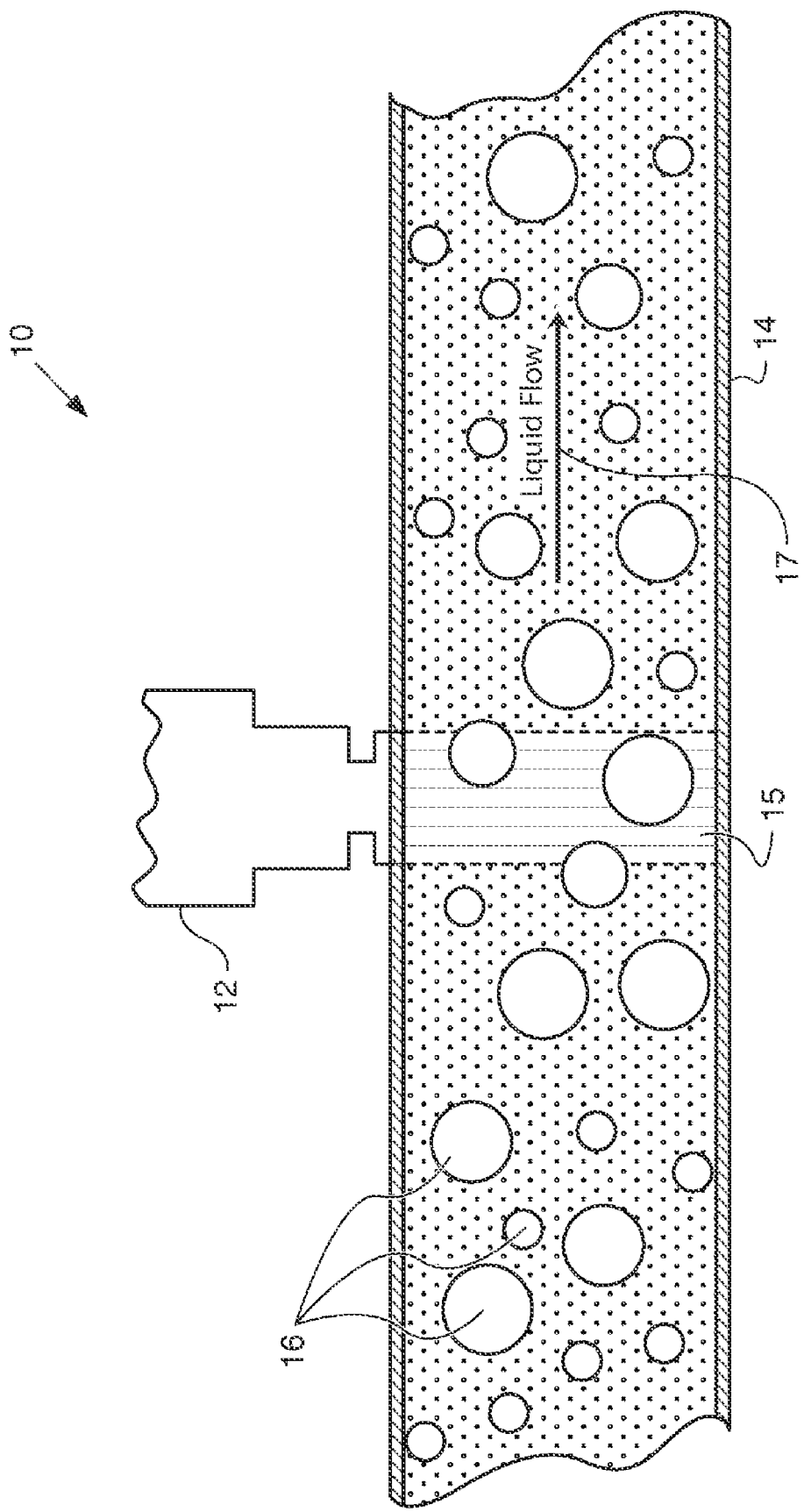

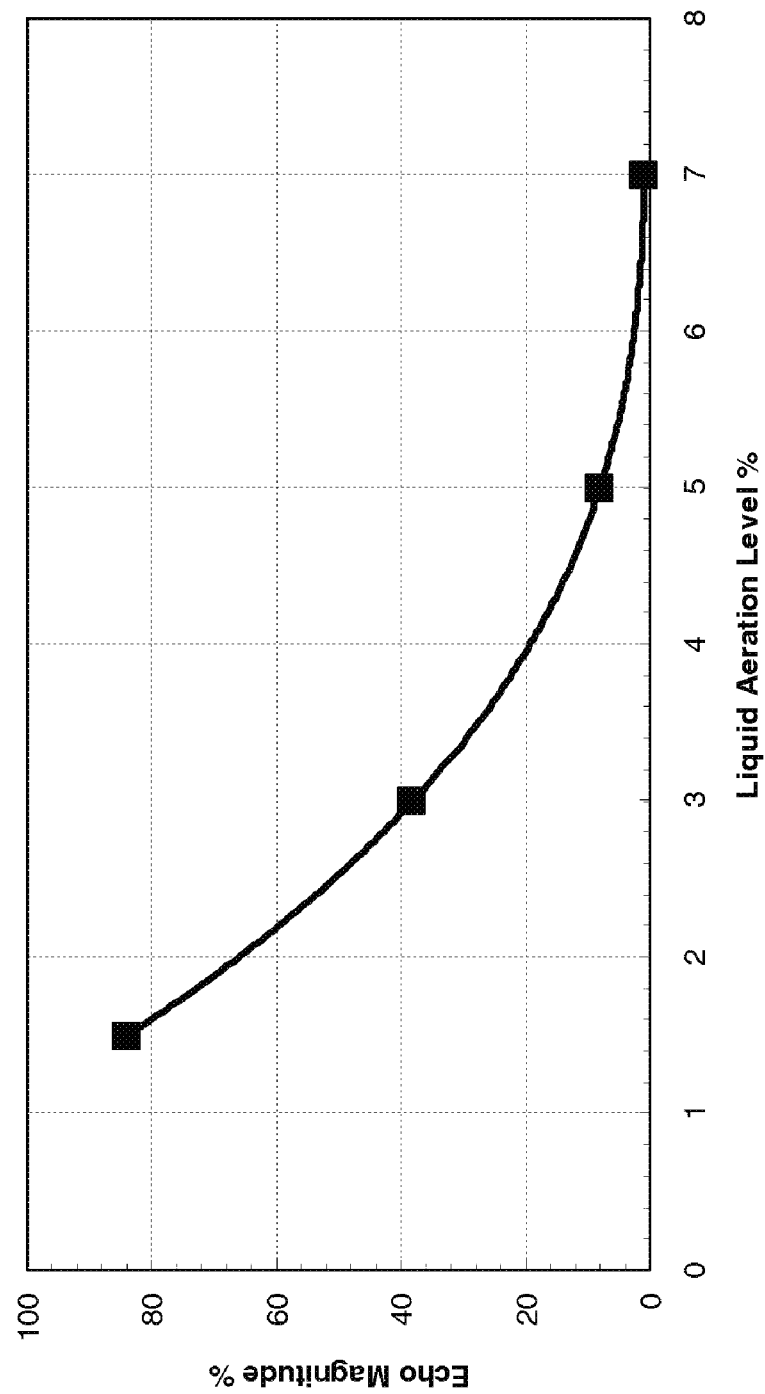

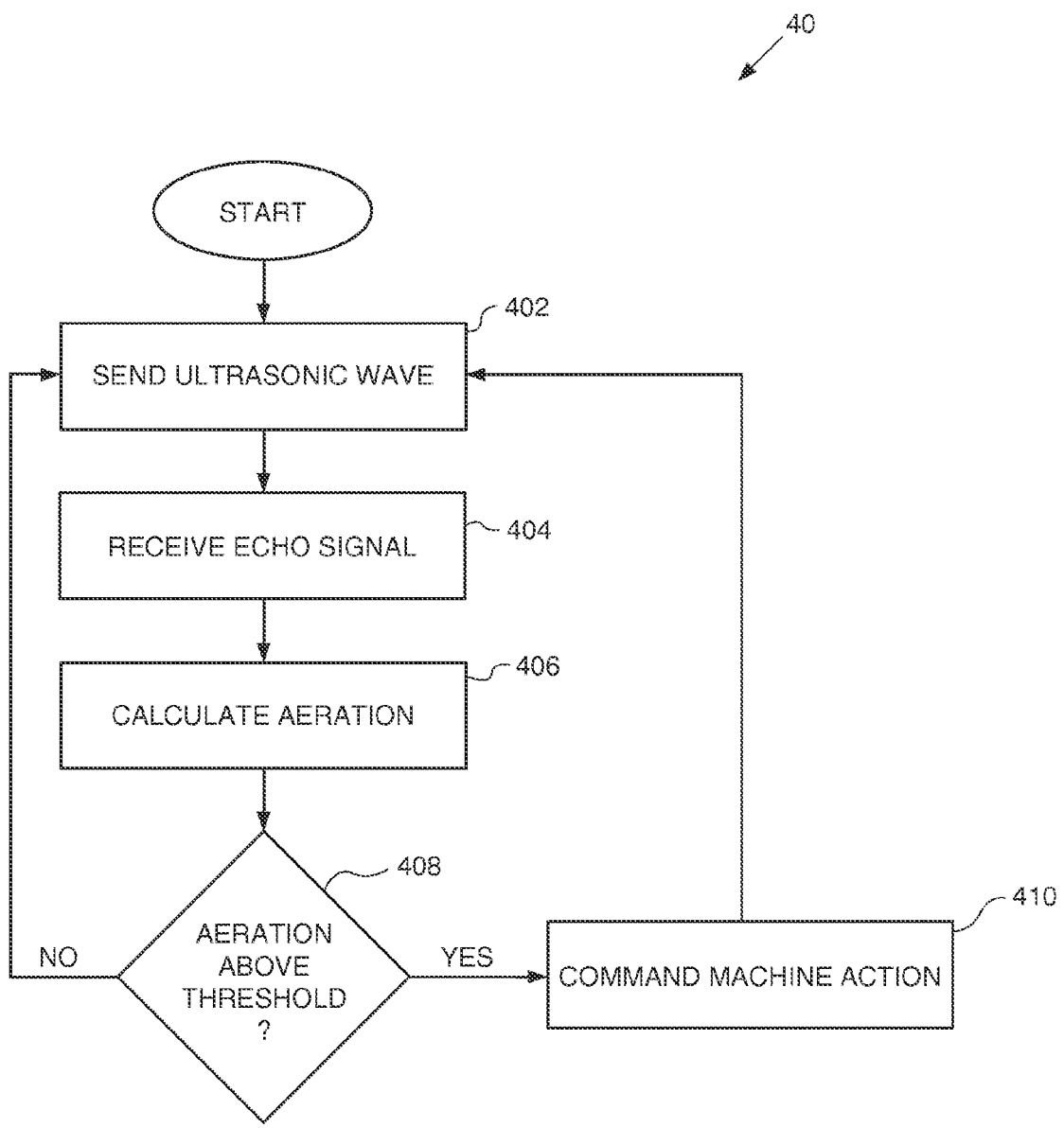

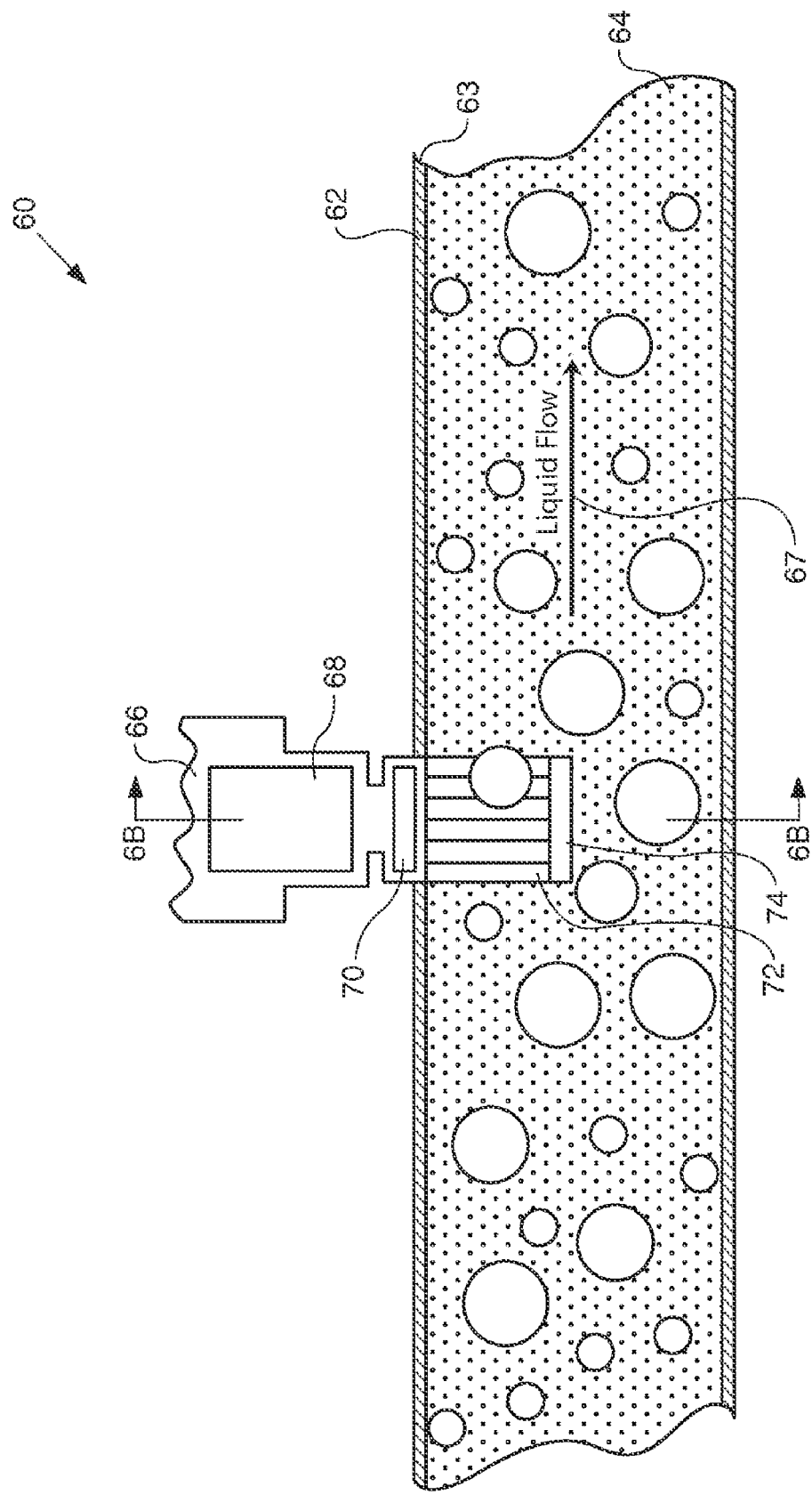

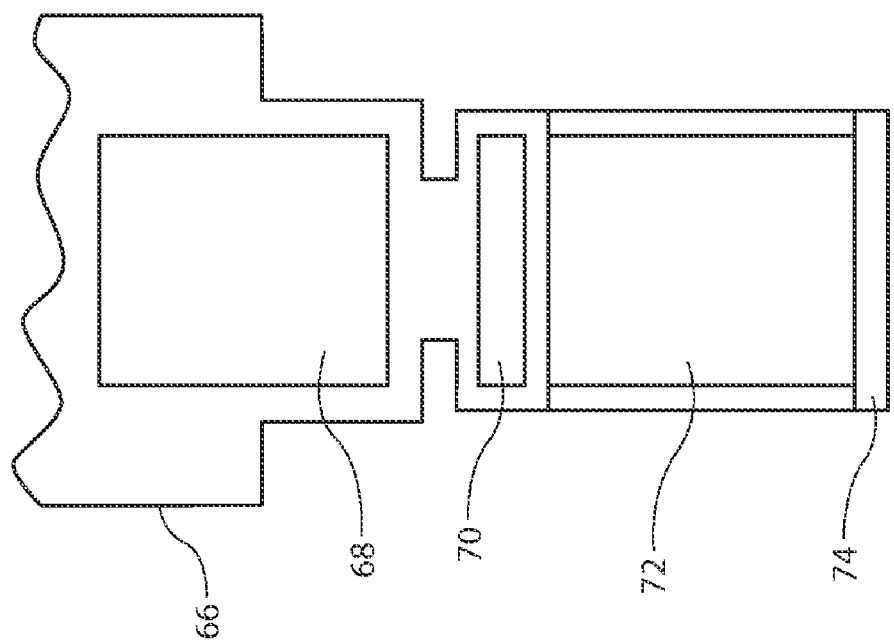

SYSTEM AND METHOD FOR MEASURING AERATION OF A LIQUID

TECHNICAL FIELD

This disclosure relates generally to a system and method for measuring the aeration of a liquid in a liquid channel. More specifically, the disclosed system and method measure the reflection of an ultrasonic wave in a liquid channel, in order to calculate the level of aeration in the liquid.

BACKGROUND

Air may exist in a liquid in three different forms. One form is "free air," which is the trapped air in a system but not totally in contact with the liquid; such as air pockets. Another form is "entrained air," which exists in the form of bubbles in the body of the liquid, while the third form is "dissolved air" that is totally mixed with the liquid and exists at the molecular level. Free and entrained air usually get into the system through different means, such as violent agitation, a leak in a connection or seal, or the release of dissolved air due to a pressure drop (e.g., at pump inlets).

It is well known that the presence of air (or other gases) in a system, such as a hydraulic system, adversely impacts the performance of the system. First, air reduces the efficiency and consistency of a hydraulic liquid in transferring energy. Second, the movement of the air through one or more liquid channels in the system can cause unwanted noise. Third, air disrupts the expected heat transfer properties of the system. Other problems of aeration in a liquid channel include: changing the natural frequency of the system, the loss of lubricity, oxidation of system components, and excessive wear on system components (e.g., pumps). Premature failure of system components leads to increased service cost and greater operational downtime for machines.

For these reasons, methods and systems exist in the art to measure the aeration of a liquid. Aeration may be calculated according to the following equation:

$$\text{Aeration \%} = \frac{\text{Total Air Volume (entrained + dissolved)}}{\text{Liquid Volume}} \times 100\%$$

The measured values in the above equation may be normalized to the standard temperature (20° C.) and atmospheric pressure if desired. Although the aeration may be defined and calculated based on both entrained and dissolved air, dissolved air may have negligible effect on liquid properties unless dissolved air is released and forms air bubbles (entrained air) in the liquid body.

There are several existing methods that are capable of quantifying entrained air in liquids. One method includes taking a sample of the liquid and then measuring the change in volume of the liquid as the air is allowed to escape from the sample. Other methods include the use of an infrared source focused on a liquid sample. U.S. Pat. No. 5,455,423 to Mount et. al. focuses an infrared source onto a venturi in a sample tube. The venturi is illuminated by the infrared source to detect and measure the amount of air bubbles in the liquid. Other methods to measure aeration known in the art include using X-rays to measure the density of the liquid. Still other methods examine the speed, temperature, and attitude of an engine relative to an axis (e.g., U.S. Pat. No. 6,758,187).

While these methods may detect the aeration of a liquid (specifically, the level of entrained air) to an adequate degree for some purposes, they have drawbacks. First, these methods require sampling the liquid from a working system to measure aeration. This often requires stopping the normal operation of the system or machine. Second, these methods may be costly. Third, the experimental setup of these methods may limit the ability to measure aeration levels at a specific location on a liquid system during normal operating conditions of a machine.

The present disclosure is directed to mitigating or eliminating one or more of the drawbacks discussed above.

SUMMARY

A method for measuring aeration of a liquid in a liquid channel is disclosed. In one exemplary embodiment, the method includes the steps of sending an ultrasonic wave into a liquid channel, and receiving a signal corresponding to the echo from the liquid channel wall. The method also includes the step of calculating a level of aeration of the liquid in the liquid channel based on the received signal In one aspect, a system for measuring the aeration of a liquid in a liquid system of a machine is disclosed. The system includes an ultrasonic transmitter configured to engage a liquid channel and an ultrasonic receiver configured to engage the liquid channel. The ultrasonic receiver receives a reflection of an ultrasonic wave from the liquid channel corresponding to an ultrasonic wave sent by the ultrasonic transmitter. The system also includes a controller operably connected to the ultrasonic receiver, wherein the controller is configured to calculate the aeration of the liquid channel based upon the signal from the ultrasonic receiver.

In another aspect, a machine includes a liquid pump, a liquid channel, an ultrasonic transmitter proximate the liquid channel, and a controller to calculate the level of aeration in the liquid channel based on the data received from the ultrasonic transmitter, including a signal corresponding to the magnitude of an echo from the liquid channel from an ultrasonic wave sent by the ultrasonic transmitter.

BRIEF DESCRIPTION OF THE DRAWINGS

FIG. 1 is a schematic illustration of an ultrasonic transmitter and an ultrasonic receiver engaging a liquid channel.

FIG. 3 is a graph comparing the magnitude of echoes with the level of aeration within a liquid of a liquid channel.

FIG. 4 is a flowchart of a method that may be used to determine the level of aeration of a liquid in a liquid channel.

FIG. 6 is a schematic illustration of a configuration of a system that may be used to determine the level of aeration of a liquid in a liquid channel.

DETAILED DESCRIPTION

Figure 2A:
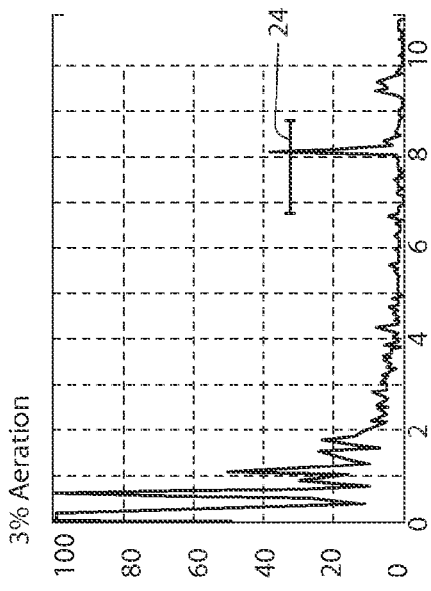
FIG. 2 is a set of graphs illustrating signals received by an ultrasonic receiver corresponding to echoes from a liquid channel.

FIG. 1 shows an exemplary system 10 for measuring the aeration of a liquid. In system 10, transducer 12 is mounted to liquid channel 14. Transducer 12 is capable of sending and receiving an ultrasonic wave 15 in liquid channel 14. Ultrasonic transducers are well known and are employed in various fields of use, including medical ultrasonography, sonar technology, and industrial nondestructive testing. For purposes of this disclosure, a "transducer" is an electromechanical device, combined in one operable unit (e.g., combined in the same housing), capable of sending an ultrasonic wave under electrical excitation and also receiving an ultrasonic echo and converting it into an electric voltage. Systems and methods according to this disclosure may be performed by a single ultrasonic transducer or by a combination of an ultrasonic transmitter and an ultrasonic receiver. In order to detect an echo from the liquid channel 14, the ultrasonic receiver will preferably be mounted in substantially the same orientation as the ultrasonic transducer, facing substantially the same area on the opposite liquid channel wall.

Liquid channel 14 may be part of a larger liquid carrying system. For example, liquid channel 14 may be part of any larger liquid carrying system on a machine, in which measurement of the level of aeration of the liquid may be desirable. The liquid channel 14 may be part of a hydraulic system carrying typical hydraulic liquid. Alternatively, liquid channel 14 may be part of a cooling system, carrying water or other typical cooling liquids. Liquid channel 14 may also be a component of an engine, carrying oil. Though it is preferable that liquid channel 14 shown in FIG. 1 is part of a system on a machine, such as a motor vehicle or construction machine, liquid channel 14 may also be a stand-alone channel for the purpose of measuring the aeration level of a liquid. In this way, the systems and methods disclosed herein may be used as part of a test apparatus, in a laboratory or at a service station, or on a service truck.

As shown, liquid channel 14 contains a liquid 17 (for example, oil) flowing from left to right. Liquid channel 14 may also contain air bubbles 16 in the liquid. As the liquid flows through liquid channel 14, transducer 12 may emit one or more ultrasonic waves, and measure the magnitude of the echo received.

FIG. 2 is a set of graphs illustrating signals received by an ultrasonic receiver corresponding to echoes from a liquid channel. The example graphs show the magnitude of the ultrasonic echo received (vertical axis) versus distance from the transducer (in divisions, horizontal axis) for a known level of aeration of a liquid (indicated above each graph).

The ultrasonic measurement instruments may display the signal from the sensor as voltage versus time (from sending of the ultrasonic wave). However, since speed of the ultrasonic waves in a particular liquid and the time delay in measurement system can be determined (typically through a calibration procedure), the time axis can also be converted to be a distance axis that are measured in divisions. Converting to distance axis may make it easier to see where a reflection occurred in the liquid channel relative to the ultrasonic transducer. One may use the following equation to determine the distance represented by each division:

$$\text{Distance per division} = \frac{(\text{sound speed in liquid}) \times \left(\begin{array}{c}\text{time of end point of display} - \\ \text{system delay}\end{array}\right)}{2 \times (\text{total \# of divisions})}$$

For example, if each division in FIG. 2 represents 0.2 inches of distance in the liquid channel, then a strong echo occurring at 8 divisions means that the echo was reflected from an object 1.6 inches (8*0.2") from the transducer surface. If that distance represents the diameter of the liquid channel, then one is assured that the echo at 8 divisions in FIG. 2 is from the opposite side of the liquid channel.

For the exemplary test shown in FIG. 2, a known level of air was added to a liquid (oil), measured using known methods (to within a measurement error of approximately plus or minus 0.5%). The air was allowed to reach a near steady-state condition in the circulating liquid channel. Then, the ultrasound reading was taken.

As shown in the graphs, after an ultrasonic pulse or wave was sent through the liquid channel, in all graphs a strong echo was received in the first few divisions (e.g., 0 to 4). This represents the echo from the surface of the liquid channel immediately near the transducer. More importantly, the level of oil aeration can be measured in this example, however, by examining the magnitude of the echo at approximately 8 divisions. This echo represents the strength of the echo received from the surface of the wall of the liquid channel opposite the transducer.

Figure 2B:
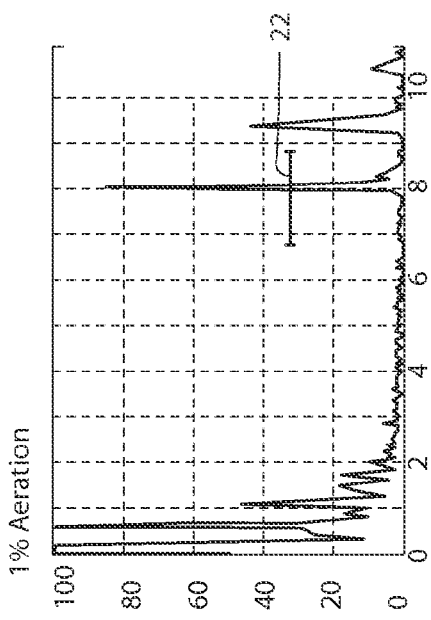
Figure 2C:
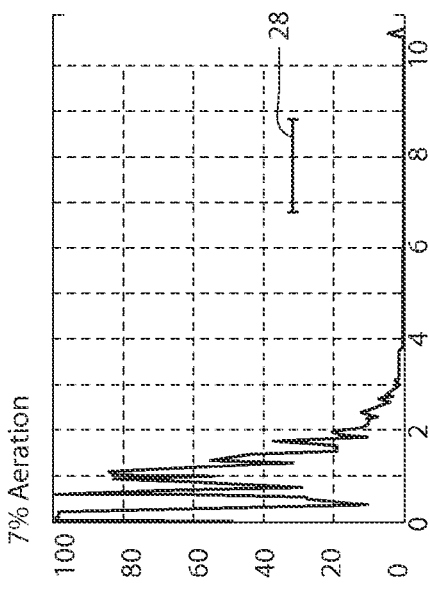
Figure 2D:
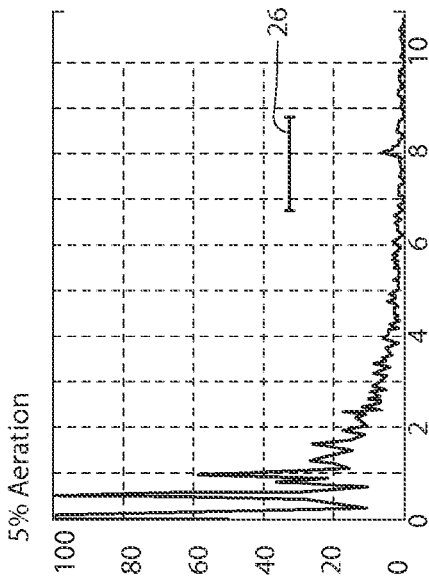

In the example of FIG. 2a, when the liquid has almost no aeration, a strong echo can be detected in range 22 at approximately 8 divisions from the transducer (the opposite side of the liquid channel). In FIG. 2b, at slightly higher level of aeration (3%), an echo can be detected in range 24, although the magnitude of the echo is weaker than in FIG. 2a, because of the higher level of aeration in the liquid. In FIG. 2c, at 5% aeration, only a very small echo is shown at range 26. Finally, in FIG. 2d, at 7% aeration, there is no noticeable echo at all in range 28.

As the graphs in FIG. 2 show, the magnitude of the ultrasonic echo received may vary, where a stronger echo from the opposite side of the liquid channel may be indicative of a lower level of aeration of the liquid. Factors other than aeration may affect the magnitude of the ultrasonic echo. For example, different types of liquids can have different viscosities and therefore will cause different attenuations to an ultrasonic wave. So the type of liquid may be required information for aeration measurement. In addition, temperature may affect liquid properties. The ultrasonic transducer may have an integrated temperature sensor. The aeration level is determined based on the output of the ultrasonic transducer at specific temperatures. However, despite these variations, a numerical value for the actual aeration of the liquid in a liquid channel may be obtained by comparing the magnitude of the echo received against the magnitude of the echo occurring for a known, reference level of liquid aeration, under a known set of reference conditions.

In this manner, the method and systems of the present disclosure may be used to obtain the level of aeration of a liquid in a variety of different system configurations. For example, liquid channel 14 may be of varying shape or diameter, or may contain a variety of liquids, or may be fabricated with varying material and wall thickness. Some of these factors might influence the exact nature of the data on both the X-axis and Y-axis of a graph such as in FIG. 2. However, comparing the results of the magnitude of an ultrasonic echo against a reference case, with known levels of liquid aeration, allows methods of the present disclosure to be adaptable to a wide variety of systems.

FIG. 3 is a graph comparing the magnitude of echoes with the level of aeration within a liquid of a liquid channel. FIG. 3 shows that the measure of liquid aeration can be correlated to echo magnitude using known curve-fitting techniques. This allows an estimate of the aeration in a liquid channel while limiting the amount of calibration required. In this example, the four echo magnitude measurements of FIG. 2 are sufficiently precise to create a correlation between the magnitude of the ultrasonic echo and the level of aeration of the liquid.

Note that the data shown in FIG. 3 were measured using a transducer with a specific center frequency. By changing using transducers with different center frequencies, one can change the measurement range and sensitivity of aeration level. Typically, at low frequencies the measurement range will be wide, but the sensitivity will be low. At high frequencies, typically the measurement range will be narrow, but the sensitivity will be high. In addition, the data shown in FIG. 3 were based on the magnitude of the echo. Other information obtained from signal analysis of the echo, such as the magnitude of a specific frequency component or averaged magnitude of different frequency components, may also be used or improve the accuracy of the aeration level measurement.

FIG. 4 is a flowchart of a method that may be used to determine the level of aeration of a liquid in a liquid channel. In step 402 an ultrasonic wave is sent through a liquid channel. As previously discussed, this may be accomplished by known ultrasonic transmitters or transducers. High temperature transducers may be required depending on applications. In the next step, step 404, the ultrasonic transducer or ultrasonic receiver may receive an echo from sent ultrasonic wave. In step 406, the magnitude of this echo may be used to determine the level of aeration in the liquid, as previously disclosed. In step 408, the level of calculated aeration is compared to a threshold level. For example, if method 40 is performed while a machine (e.g., a construction machine) is in operation, a threshold level of acceptable aeration in the liquid channel may be determined and a threshold set. This threshold value may be stored, for example, on board the machine electronic systems (or on off-board system in communication with the machine).

If the calculated value of aeration exceeds the threshold limit, a machine action may be commanded, step 410. The machine action may be to warn the machine operator that the level of aeration in the liquid system being monitored exceeds a threshold value. This could be accomplished in a variety of ways. For example, a warning light or other indication may alert the operator. Alternatively, the machine may automatically send a signal to a central operator station, or to a service technician or service system, that the aeration of the liquid system is above the threshold level. Alternatively, the machine action may be to disable the liquid system, a particular machine component impacted by the aeration level, or the machine itself.

The threshold value may be predetermined by the level of aeration acceptable in the machine. For example, the threshold value may be the highest level of aeration acceptable without causing undue adverse impacts on machine performance, such as excessive noise, oxidation, or loss of efficiency.

It should be noted that step 408 and step 410 are optional to method 40. In addition, a number of other optional steps may be performed to gather superior data on the impact of liquid aeration on a machine. For example, the amount of aeration in a liquid system of a machine may be stored, such as electronically onboard the machine, or sent off-board for electronic storage using any common data communication protocol (e.g., IEEE 802.11). Other machine parameters, such as temperature, engine parameters, or hydraulic system performance parameters, may be stored in addition to the liquid aeration data. These parameters may be correlated to more precisely determine the acceptable level of aeration in a liquid system.

For example, onboard, periodic measurement of the aeration in a hydraulic system, coupled with data concerning the performance and life of a hydraulic pump, may help more precisely determine the level of aeration acceptable in the system without unduly impacting the life of the pump.

Figure 5:
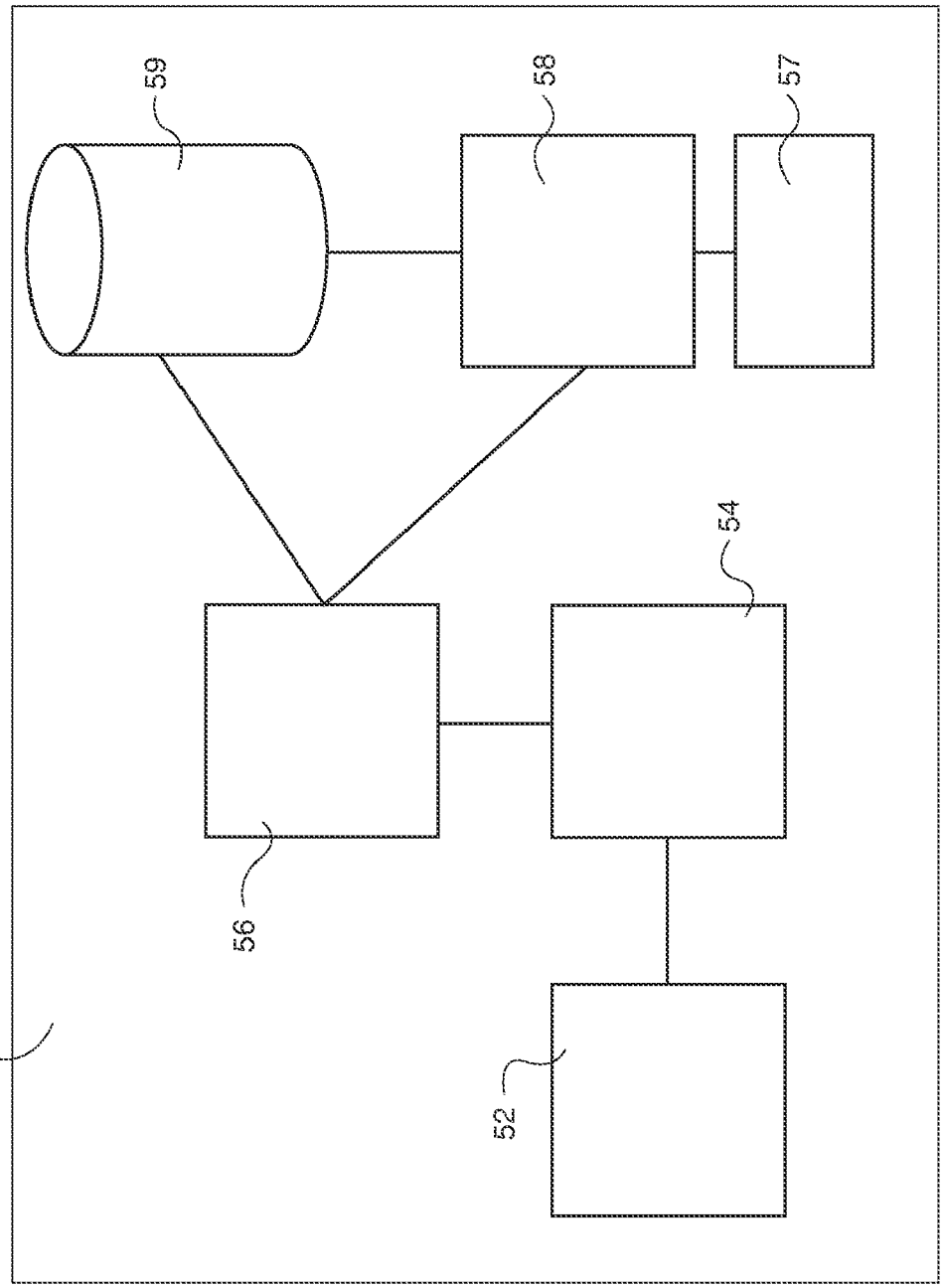
FIG. 5 is a schematic illustration of a system that may be used to determine the level of aeration of a liquid in a liquid channel.

FIG. 5 is a schematic illustration of a system that may be used to determine the level of aeration of a liquid in a liquid channel. Machine 50 includes a liquid pump 52 connected to a liquid channel 54. Liquid pump 52 can be any common pump for a hydraulic system, cooling system, oil pump, etc. Liquid channel 54 forms at least a portion of a liquid system on machine 50. Transducer 56 is mounted proximate the liquid channel 54 for taking ultrasonic measurements of the level of aeration in liquid channel 54. Transducer 56 may be operably connected to controller 58, wherein controller 58 may selectively activate transducer 56 to take an aeration measurement at a desired time. For example, controller 58 may operate transducer 56 to take aeration measurements at regular time intervals. Alternatively, controller 58 may operate transducer 56 under select machine conditions. For example, transducer 56 may take measurements of liquid channel 14 only when liquid pump 52 exceeds a threshold flow rate.

Either controller 58 and/or transducer 56 may be in communication with storage device 59, for storing the aeration data obtained by transducer 56. Storage device 59 may be any common data storage device such as a hard disk, RAM, or similar digital media. Storage device 59, though shown onboard machine 50 in FIG. 5, is not required to be onboard machine 50. Machine 50 may send aeration data off-board for analysis and storage, along with other machine data, using standard data communications protocols. In addition, controller 58 and/or storage device 59 may receive and process a machine parameter 57. Machine parameter 57 may be any data measured on the machine, such as engine parameters, hydraulic system parameters, transmission state parameters, operator command parameters, and any other data gathered by an electronic control module on the machine.

FIG. 6a shows a schematic illustration of a system 60 in accordance with another embodiment of the present disclosure. Transducer 66 includes ultrasound electronics 68 and is operably attached to liquid channel 64 containing liquid 67. In the embodiment shown, the edge of transducer 66 is aligned with liquid channel wall 62. Vibratory element 70 within transducer 66 causes ultrasonic waves to be sent within liquid channel 64.

As previously noted with respect to FIGS. 1-3, the magnitude of the ultrasonic echo received in a configuration such as FIG. 1 will vary according to factors including the physical characteristics of the liquid channel, including the width of the liquid channel and the reflective properties of the liquid channel wall. Thus, calibration of the configuration of FIG. 1 against known reference values of aeration for any particular liquid channel configuration may be desirable for accuracy.

However, FIG. 6a shows an embodiment of the present disclosure that may mitigate the need for calibration for differing liquid channels. In FIG. 6a, transducer 66 also contains a reflective element 74 extending into liquid channel 64. Reflective element 74 is connected to the main part of transducer 66 by at least one wall 72. Wall 72 runs parallel to the point of view shown in FIG. 6a, thus causing minimal or no measurable disruption to the flow of liquid in liquid channel 64. Because the reflective properties of reflective element 74 are known, and because the length of wall 72 (and thus the distance between vibratory element 70 and reflective element 74) is known, these properties no longer vary according to the properties of liquid channel 64. This allows transducer 66 to be inserted into liquid channels of various sizes and materials while allowing consistent measurement of the aeration of the liquid in the liquid channel, without the calibration required to take into account the liquid channel properties.

FIG. 6b shows a cross section of transducer 66 shown in FIG. 6a. Two walls 72 and reflective element 74 collectively form a hollow cavity through which liquid may flow when placed in a liquid channel, such as liquid channel 64 shown in FIG. 6a. Vibratory element 70 incites ultrasonic waves that are reflected off reflective element 74, and the magnitude of the echo may be measured to determine the level of aeration in the liquid.

INDUSTRIAL APPLICABILITY

The present disclosure provides advantageous systems and methods for measuring the level of aeration of a liquid in a liquid channel. Embodiments of the present disclosure may be used in a variety of different liquid carrying systems of various configurations. In addition, the embodiments disclosed herein may be configured for use as a stand-alone service tool, or embedded on a machine to measure aeration during normal operation of the machine. They may be advantageous over prior art systems in the ability to measure the aeration of a liquid with lower cost equipment, with a less complicated equipment setup. In addition, embodiments of the disclosure may allow an operator to access and measure the aeration on a liquid channel which is less accessible to measurement via prior art techniques of measuring liquid aeration. For example, the techniques disclosed herein may allow for equipment to be placed on only one side of a liquid channel, and do not require extracting and sampling the liquid for measurement.

In general, a method for measuring aeration of a liquid involves sending at least one ultrasonic wave into a liquid channel, and then receiving a signal corresponding to an echo from a liquid channel wall. The level of aeration of the liquid in the liquid channel is calculated based on the magnitude of the reflected signal. Optionally, the level of aeration of the liquid is compared to a threshold value of liquid aeration, and a machine action may be commanded if the level of aeration exceeds the threshold value. This machine action may include warning the operator. In addition, data relating to the level of aeration of the liquid may be stored, along with other machine parameters, and the data correlated for analysis and machine diagnostics.

In addition, a system for measuring the aeration of a liquid in a machine includes an ultrasonic transmitter and an ultrasonic receiver configured to engage a liquid channel. The ultrasonic transmitter and ultrasonic receiver may be mounted facing substantially the same area on the opposite liquid channel wall, or optionally contained in the same housing (i.e., a transducer). The ultrasonic receiver receives a reflection of an ultrasonic wave from the liquid channel corresponding to an ultrasonic wave sent by the ultrasonic transmitter. A controller calculates the aeration of the liquid channel based upon the signal from the ultrasonic receiver. The controller (along with the ultrasonic transmitter and ultrasonic receiver) may be mounted on a machine containing the liquid channel for measurement during the machine's operation. Optionally, the data relating to aeration of the liquid may be stored for later recall and analysis. In addition, the system may include a reflective element as part of the measurement unit, in order to obtain more consistent results without further calibration. The ultrasonic transmitter and ultrasonic receiver may be selectively activated to obtain data at desired times. The machine may include a liquid pump that circulates liquid through the liquid channel being measured (for example, a hydraulic pump).

Other embodiments, features, aspects, and principles of the disclosed examples will be apparent to those skilled in the art and may be implemented in various environments and systems.

What is claimed is:

1. A system for measuring aeration of a liquid in a machine, comprising:
    an ultrasonic transmitter configured to engage a liquid channel;
    an ultrasonic receiver configured to engage the liquid channel;
    wherein the ultrasonic receiver receives a reflection of an ultrasonic wave corresponding to an ultrasonic wave sent by the ultrasonic transmitter; and
    a controller operably connected to the ultrasonic receiver, wherein the controller is configured to calculate the aeration of the liquid channel based upon the signal from the ultrasonic receiver and command a machine action if the aeration of the liquid channel exceeds a threshold value of liquid aeration;
    wherein the machine is selected from a group including a motor vehicle and a construction machine; and
    wherein the controller is further configured to divide the width of the liquid channel into a plurality of divisions, and to calculate the aeration of the liquid channel based upon the signal received corresponding to one of the plurality of divisions.

2. The system of claim 1, wherein the ultrasonic transmitter and the ultrasonic receiver are combined in the same housing.

3. The system of claim 1, wherein the ultrasonic receiver and the ultrasonic transmitter are mounted facing substantially the same area on the opposite liquid channel wall.

4. The system of claim 3, wherein the controller, the ultrasonic transmitter, and the ultrasonic receiver are mounted on a machine containing the liquid channel.

5. The system of claim 1, wherein the aeration is determined from a reflection of an ultrasonic wave from the liquid channel wall substantially opposite the ultrasonic transmitter.

6. The system of claim 1, including a reflective element.

7. The system of claim 6, including a wall connecting the reflective element to a housing of one of the ultrasonic transmitter or the ultrasonic receiver.

8. The system of claim 1, wherein the machine action includes at least one of disabling a liquid system, disabling a particular machine component impacted by the aeration of the liquid, or disabling the machine.

9. A machine comprising:
    a liquid pump;
    a liquid channel;
    an ultrasonic transducer proximate the liquid channel,
    a reflective element operably attached to the ultrasonic transducer,
    a controller to calculate the level of aeration in the liquid channel based on data received from the ultrasonic transducer, including a magnitude of an echo from the liquid channel from an ultrasonic wave sent by the ultrasonic transducer;
    wherein the machine is selected from a group including a motor vehicle and construction machine; and
    wherein the reflective element is located in the liquid channel.

10. The machine of claim 9, including data storage device for storing the level of aeration.

11. The machine of claim 9, wherein the controller is further configured to selectively activate the ultrasonic transmitter and the ultrasonic receiver.

* * * * *